US005084142A

United States Patent [19]

Berg et al.

[11] Patent Number: 5,084,142

[45] Date of Patent: Jan. 28, 1992

[54] SEPARATION OF TERTIARY BUTYL ALCOHOL FROM WATER BY AZEOTROPIC OR EXTRACTIVE DISTILLATION

[75] Inventors: Lloyd Berg, 1314 S. Third Ave., Bozeman, Mont. 59715; Zuyin Yang, both of Bozeman, Mont.

[73] Assignee: Lloyd Berg, Bozeman, Mont.

[21] Appl. No.: 658,504

[22] Filed: Feb. 21, 1991

[51] Int. Cl.[5] .......................... B01D 3/36; B01D 3/40; C07C 29/84

[52] U.S. Cl. ...................................... 203/18.0; 203/57; 203/60; 203/62; 203/63; 203/64; 568/916

[58] Field of Search ........................ 203/63, 62, 60, 57, 203/64, 56, 51, 18; 568/916, 918

[56] References Cited

U.S. PATENT DOCUMENTS 2,140,694 12/1938 Evans .................................... 203/63
2,559,519 7/1951 Smith et al. ............................ 203/64
2,591,671 4/1952 Catterall ................................ 203/63
3,464,896 9/1969 Washall ................................. 203/64
4,366,032 12/1982 Mikitenko et al. .................... 203/18
4,400,241 8/1983 Braithwaite et al. .................. 203/64
4,631,115 12/1986 Berg et al. ............................ 203/51
4,636,284 1/1987 English et al. ........................ 203/64

*Primary Examiner*—Wilbur Bascomb, Jr.

[57] ABSTRACT t-Butyl alcohol cannot be completely separated from water by conventional distillation or rectification because of the minimum boiling azeotrope. t-Butyl alcohol can be readily separated from water by using azeotropic or extractive distillation. Typical examples of effective agents are: by azeotropic distillation, vinyl n-butyl ether and propylene glycol dimethyl ether; by extractive distillation, 1,3-butanediol and triethylene glycol.

4 Claims, No Drawings

SEPARATION OF TERTIARY BUTYL ALCOHOL FROM WATER BY AZEOTROPIC OR EXTRACTIVE DISTILLATION

FIELD OF THE INVENTION

This invention relates to a method for separating t-butyl alcohol from water using certain organic compounds as the agent in azeotropic or extractive distillation.

DESCRIPTION OF PRIOR ART

Extractive distillation is the method of separating close boiling compounds or azeotropes by carrying out the distillation in a multi-plate rectificatic column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Calcius degrees or more higher than the lower boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

t-Butyl alcohol, B.P.=82.5° C. forms a minimum boiling azeotrope with water at 79.9° C. containing 11.8% water. The t-butyl alcohol - water azeotrope is impossible to separate by distillation because the relative volatility is 1.0. Extraction distillation would be an attractive method of effecting the separation of t-butyl alcohol from water if agents can be found that (1) will enhance the relative volatility between t-butyl alcohol and water and (2) are easy to recover, that is, form no azeotrope with t-butyl alcohol or water and boil sufficiently above these two to make separation by rectification possible with only a few theoretical plates. Azeotropic distillation would also be an attractive method of separating these two if agents can be found that will enhance the relative volatility sufficiently.

The advantage of using azeotropic or extractive distillation in this separation can be seen from the data presented in Table 1 below.

TABLE 1

Theoretical And Actual Plates Required vs. Relative Volatility

| Relative Volatility | Theoretical Plates Required At Total Reflux, 99% Purity | Actual Plates Required, 75% Eff. |
|---|---|---|
| 1.2 | 52 | 70 |
| 1.5 | 23 | 31 |
| 2.0 | 13 | 17 |
| 2.5 | 10 | 13 |

The relative volatility of the t-butyl alcohol-water azeotrope is 1 and thus cannot be separated by conventional rectification. Plates possessing an efficiency of 75% are commonly employed. Several of the agents that we have discovered yield a relative volatility of 2.0 or higher which would require a plate requirement of only 17.

Extractive distillation typically requires the addition of an equal amount to twice as much extractive agent as the propanol-water mixture on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable also that the extractive agent be miscible with the t-butyl alcohol otherwise it will form a two-phase azeotrope with the t-butyl alcohol in the recovery column and some other method of separation will have to be employed.

OBJECTIVE OF THE INVENTION

The objects of this invention are to provide a process or method of azeotropic or extractive distillation that will enhance the relative volatility of t-butyl alcohol from water in their separation in a rectification column. It is a further object of this invention to identify organic compounds that are stable, can be separated from the t-butyl alcohol by rectification with relatively few plates and can be recycled to the extractive distillation column with little decomposition.

SUMMARY OF THE INVENTION

The objects of this invention are provided by a process for the separation of t-butyl alcohol from water which entails the use of certain organic compounds as the agent in azeotropic or extractive distillation.

DETAILED DESCRIPTION OF THE INVENTION

We have discovered that certain organic compounds will effectively increase the relative volatility between t-butyl alcohol and water and permit the separation of t-butyl alcohol from water by rectification when employed as the agent in azeotropic or extractive distillation. Table 2 lists the agents that we have found to be effective azeotropic distillation agents to recover water as the overhead product from t-butyl alcohol. One agent, propylene glycol dimethyl ether brings out the t-butyl alcohol as overhead. The data listed in Tables 2 and 3 was obtained in a vapor-liquid equilibrium still. In every case, the starting material was the t-butyl alcohol-water azeorrope. The relative volatilities are listed for each of the agents. The compounds which are effective azeotrope formers to remove water as overhead from t-butyl alcohol are hexyl acetate, 3-methyl-2-pentanone, 3-heptanone, nm-butyl ether and vinyl isobutyl ether.

Table 3 lists the compounds that are effective extractive distillation agents. The compounds which bring out the water as the overhead product are hexylene glycol, 1,2-butanediol, polyethylene glycols 200 and 300, anisole, diisobutyl ketone, n-butyl acetate, propoxypropanol, hexyl alcohol, undecyl alcohol, isodecanol, alpha-methyl benzyl alcohol, cyclododecanol, diisobutyl carbinol, 2-octanol, methyl isoamyl ketone, 3-heptanone, diethylene glycol diethyl ether, 3-octanone, isophorone, 2-hydroxyacetophenone, 2-undecanone, mesityl oxide, benzyl benzoate, ethylene glycol diacetate, ethyl salicylate, 3-hexanone, ethylene glycol phenyl ether, isobutyl butyrate, ethylene glycol butyl ether, ethyl butyrate, methyl caproate, amyl propionate and ethyl n-valerate. The compounds which bring out the t-butyl alcohol was overhead product are 1,3-butanediol, 1,4-butanediol, dipropylene glycol, triethylene glycol, 2-methyl-1,3-propanediol, diethylene glycol, polyethylene glycol 400, tetraethylene glycol, methyl benzoate, dimethyl sulfoxide, dimethyl formamide, dimethyl phthalate and dimethyl adipate.

Table 4 lists a number of compounds that proved to be ineffective as extractive distillation agents in the separation of t-butyl alcohol from water.

Three of the agents whose relative volatility had been determined in the vapor-liquid equilibrium still were then evaluated in a glass perforated plate rectification column possessing 7.3 theoretical plates and the results listed in Table 5. Vinyl n-butyl ether was evaluated in the azeotropic distillation mode and gave a relative volatility of 1.50. 1,3,Butanediol and triethylene glycol were evaluated in the extractive distillation mode and yielded relative volatilities of 1.178 and 1.235 respectively.

TABLE 2

Effective Azeotropic Agents For Separating Water From t-Butanol

| Compounds | Relative Volatility |
|---|---|
| Hexyl acetate | 2.0 |
| 3-Methyl-2-pentanone | 1.55 |
| 2-Heptanone | 1.42 |
| n-Butyl ether | 2.4 |
| Vinyl isobutyl ether | 3.5 |
| Propylene glycol dimethyl ether | 1.9* |

*Brings t-butanol out as overhead

TABLE 3

Effective Extractive Agents For Separating Water From t-Butanol

| Compounds | Relative Volatility |
|---|---|
| Hexylene glycol | 1.28 |
| 1,2-Butanediol | 1.30 |
| 1,3-Butanediol | 1.20* |
| Polyethylene glycol 200 | 1.95 |
| Polyethylene glycol 300 | 1.34 |
| 1,4-Butanediol | 1.38* |
| Dipropylene glycol | 1.32* |
| Triethylene glycol | 2.33* |
| 2-Methyl-1,3-propanediol | 1.32* |
| Diethylene glycol | 1.26* |
| Polyethylene glycol 400 | 1.92* |
| Tetraethylene glycol | 1.28* |
| Methyl benzoate | 1.21* |
| Anisole | 1.31 |
| Diisobutyl ketone | 1.42 |
| n-Butyl acetate | 1.47 |
| Propoxypropanol | 1.41 |
| Hexyl alcohol | 1.70 |
| Undecyl alcohol | 1.25 |
| Isodecanol | 1.63 |
| alpha-Methyl benzyl alcohol | 1.36 |
| Cyclododecanol | 1.47 |
| Diisobutyl carbinol | 1.94 |
| 2-Octanol | 1.47 |
| Methyl isoamyl ketone | 1.61 |
| 3-Heptanone | 1.70 |
| Diethylene glycol diethyl ether | 1.44 |
| Dimethyl sulfoxide | 1.51* |
| 3-Octanone | 2.0 |
| 2-Hydroxyacetophenone | 1.32 |
| Dimethyl formamide | 1.35* |
| Isophorone | 1.54 |
| 2-Undecanone | 1.33 |
| Mesityl oxide | 1.83 |
| Benzyl benzoate | 1.28 |
| Ethylene glycol diacetate | 1.23 |
| Ethyl salicylate | 1.32 |
| 3-Hexanone | 1.97 |
| Ethylene glycol phenyl ether | 2.49 |
| Isobutyl butyrate | 1.22 |
| Ethylene glycol butyl ether | 1.21 |
| Ethyl butyrate | 1.62 |
| Methyl caproate | 2.07 |
| Amyl propionate | 1.41 |
| Ethyl n-valerate | 1.38 |
| Dimethyl phthalate | 1.41* |
| Dimethyl adipate | 1.21* |

*Brings t-butanol out as overhead

TABLE 4

| Ineffective Agents For Separating Water From t-Butanol | |
|---|---|
| Tripropylene glycol | 1,5-Pentanediol |
| 1,6-Hexanediol | Butoxypropanol |
| Nonyl alcohol | Isononyl alcohol |
| 2-Ethyl-1-hexanol | Benzyl alcohol |
| 2,4-Pentanedione | Isobutyl heptyl ketone |
| Vinyl butyl ether | Diethylene glycol t-butyl ether methyl ether |
| 2-Methoxyethyl ether | Dimethylacetamide |
| Adiponitrile | Ethylene glycol methyl ether acetate |
| Benzyl acetate | Methyl salicylate |
| Glyceryl triacetate | Diethylene glycol butyl ether acetate |
| Triethylene glycol diacetate | Ethylene glycol ethyl ether acetate |
| Diethyl malonate | Diethylene glycol ethyl ether acetate |
| Dihexyl phthalate | Methyl heptanoate |
| Diethyl phthalate | |

TABLE 5

Data From Runs Made In Rectification Column - t-butanol From Water

| Agent | Column | Time hrs. | Weight % t-Butanol | Weight % Water | Weight % Agent | Relative Volatility | Mode |
|---|---|---|---|---|---|---|---|
| Vinyl n-butyl | Overhead | 9 | 32.7 | 9.1 | 58.2 | 1.50 | Azeotropic |

TABLE 5-continued

| | Data From Runs Made In Rectification Column - t-butanol From Water | | | | | | |
|---|---|---|---|---|---|---|---|
| Agent | Column | Time hrs. | Weight % t-Butanol | Weight % Water | Weight % Agent | Relative Volatility | Mode |
| ether | Bottoms | | 69.9 | 1.0 | 29.1 | | |
| 1,3-Butanediol | Overhead | 2 | 94.7 | 5.3 | — | 1.178 | Extractive |
| | Bottoms | | 84.4 | 15.6 | | | |
| Triethylene | Overhead | 1 | 95 | 5 | — | 1.235 | Extractive |
| glycol | Bottoms | | 80.2 | 19.8 | | | |

THE USEFULNESS OF THE INVENTION

The usefulness or utility of this invention can be demonstrated by referring to the data presented in Tables 2 to 5. All of the successful agents show that t-butyl alcohol can be separated from water by means of azeotropic or extractive distillation in a rectification column and that the ease of separation as measured by relative volatility is considerable.

WORKING EXAMPLES

Example 1

Forty grams of the t-butyl alcohol-water azeotrope and 30 grams of vinyl isobutyl ether as the azeotrope former were charged to a vapor-liquid equilibrium still and refluxed for ten hours. Analysis indicated a vapor composition of 15.9% water, 84.1% t-butyl alcohol; a liquid composition of 5.1% water, 94.1% t-butyl alcohol which is a relative volatility of 3.5.

Example 2

Eighty grams of the t-butyl alcohol-water azeotrope and 30 grams of propylene glycol dimethyl ether as the azeotrope former were charged to the vapor-liquid equilibrium still and refluxed for ten hours. Analysis indicated a vapor composition of 10.3% water, 89.7% t-butyl alcohol; a liquid composition of 18.4% water, 81.6% t-butyl alcohol which is a relative volatility of t-butyl alcohol to water of 1.9.

Example 3

Eighty grams of the t-butyl alcohol-water azeotrope and 30 grams of ethylene glycol phenyl ether were charged to the vapor-liquid equilibrium still and refluxed for fourteen hours. Analysis indicated a vapor composition of 23.3% water, 76.8% t-butyl alcohol; a liquid composition of 10.8% water, 89.2% t-butyl alcohol which is a relative volatility of 2.49.

Example 4

Eighty grams of the t-butyl alcohol-water azeotrope and 30 grams of dimethyl phthalate were charged to the vapor - liquid equilibrium still and refluxed for one hour. Analysis indicated a vapor composition of 14.8% water, 85.2% t-butyl alcohol; a liquid composition of 19.7% water, 80.3% t-butyl alcohol which is a relative volatility of t-butyl alcohol to water of 1.41.

Example 5

Two hundred grams of the t-butyl alcohol-water azeotrope and 85 grams of vinyl n-butyl ether as the azeotrope former were charged to the stillpot of a 7.3 theoretical plate glass perforated tray rectification column and refluxed at total reflux for four hours. Analysis indicated a vapor composition of 4.6% water, 31.0% t-butyl alcohol, 64.4% vinyl n-butyl ether; a liquid composition of 2.1% water, 68.4% t-butyl alcohol and 29.5% vinyl n-butyl ether. This gives an average relative volatility of 1.24 for each theoretical plate. This data is presented in Table 5.

Example 6

A solution comprising 176 grams of t-butyl alcohol and 24 grams of water was placed in the stillpot of the 7.3 theoretical plate rectification column. When refluxing began, an extractive agent comprising triethylene glycol was pumped into the column at a rate of 15 ml/min. The temperature of the extractive agent as it entered the column was 85° C. After establishing the feed rate of the extractive agent, the heat input to the t-butyl alcohol-water in the stillpot was adjusted to give a total reflux rate of 40 ml/min. After one hour of operation, the overhead and bottoms samples of approximately two ml. were collected and analysed. The overhead analysis was 95% t-butyl alcohol, 5% water and the bottoms analysis was 80.22% t-butyl alcohol, 19.8% water. This gives an average relative volatility of 1.235 for each theoretical plate. This data is presented in Table 5.

We claim:

1. A method for recovering t-butyl alcohol from a mixture of t-butyl alcohol and water which comprises distilling a mixture of t-butyl alcohol and water in the presence of about one part of an extractive agent per part of t-butyl alcohol-water mixture, recovering the water as overhead product and obtaining the t-butyl alcohol and the extractive agent from the stillpot, wherein said extractive agent, consists of one material selected from the group consisting of diisobutyl ketone, n-butyl acetate, propoxypropanol methyl isoamyl ketone, 3-heptanone, 3-octanone, diethylene glycol diethyl ether, isophorone, 2-hydroxyacetophenone, 2-undecanone, mesityl oxide, benzyl benzoate, ethyl salicylate, ethylene glycol diacetate, isobutyl butyrate, ethyl butyrate, methyl caproate, amyl propionate and ethyl valerate.

2. A method for recovering t-butyl alcohol from a mixture of t-butyl alcohol and water which comprises distilling a mixture of t-butyl alcohol and water in the presence of about one part of an extractive agent per part of t-butyl alcohol-water mixture, recovering the t-butyl alcohol as overhead product and obtaining the extractive agent and the water from the stillpot, wherein said extractive agent consists of one material selected from the group consisting of methyl benzoate, dimethylsulfoxide, dimethyl formamide, dimethyl phthalate and dimethyl adipate.

3. A method for recovering t-butyl alcohol from a mixture of t-butyl alcohol and water which comprises distilling a mixture of t-butyl alcohol and water in the presence of an azeotrope forming agent, recovering the water and the azeotrope forming agent as overhead product and obtaining the t-butyl alcohol from the stillpot, wherein said azeotrope forming agent comprises one material selected from the group consisting of hexyl acetate, 3-methyl-2-pentanone and 2-heptanone.

4. A method for recovering t-butyl alcohol from a mixture of t-butyl alcohol and water which comprises distilling a mixture of t-butyl alcohol and water in the presence of an azeotrope forming agent, recovering the t-butyl alcohol and the azeotrope forming agent as overhead product and obtaining the water from the stillpot, wherein said azeotrope forming agent consists of propylene glycol dimethyl ether.

* * * * *